United States Patent [19]

Ramachandran et al.

[11] 4,415,546
[45] Nov. 15, 1983

[54] BIOLOGICALLY ACTIVE ANALOGS OF ACTH AND RADIOIMMUNO ASSAY THEREFOR

[76] Inventors: Janakiraman Ramachandran, 3279 Emerson St., Palo Alto, Calif. 94306; Douglas I. Buckley, 1379 A 5th Ave.; Donald H. Yamashiro, 1375 18th Ave. Apt. 1, both of San Francisco, Calif. 94122; James R. Hagman, 1935 Haste St. Apt. 3, Berkeley, Calif. 94704

[21] Appl. No.: 262,974

[22] Filed: May 12, 1981

[51] Int. Cl.$^3$ .................... G01N 33/56; G01N 33/58; C07C 103/52
[52] U.S. Cl. ............................. 424/1.1; 260/112.5 R; 424/9
[58] Field of Search ........................... 424/1, 8, 9, 12; 23/230 B; 260/112.5 R

[56] References Cited

PUBLICATIONS

Matsuyama et al., Endocrinol., vol. 88, Mar. 1971, pp. 696–701.
Wolfsen et al., J. Clin. Endocrinol. Met., vol. 34, Apr. 1972, pp. 684–689.
Landon, Lancet, Feb. 10, 1968, pp. 273–276.
Greenwood, Cin. Chim. Acta, vol. 22, Sep. 1968, pp. 77–78.
Marton et al., J. Endocr., vol. 78, Aug. 1978, pp. 309–319.
Matsuyama et al., J. Clin. Endocrinol. Met., vol. 34, Apr. 1972, pp. 713–717.
Properties of a Simplified Bioassay for Adrenocorticotropic Activity Using the Steroidogenic Response of Isolated Adrenal Cells by P. J. Lowry et al. in J. Endocr. (1973) 59:43–55.
Isolation, Characterization and Synthesis of a Corticotropin-Inhibiting Peptide from Human Pituitary Glands by Choh Hao Li et al. in Proc. Natl Acad. Sci. vol. 75, No. 9 pp. 4306–4309, Sep. 1978.
ACTH Receptors in The Adrenal: Specific Binding of ACTH$^{125}$ and its Relation to Adenyl Cyclase by R. J. Lefkowitz et al. in Proc. Natl. Acad. of Sci. Vol. 65, No. 3 pp. 745–752, Mar. 1970.
The Preparation of Biologically Active $^{125}$I-Labeled Adrenocorticotropic Hormone by a Simple Enzymic Radioiodination Procedure Utilizing Lactoperoxidase by J. McIlhinney et al. in Endocr. vol. 94, No. pp. 1259–1264, 19.
The Preparation and Immunological Properties of $^{131}$I-Labeled Adrenoxorticotropin by J. Landon et al. in Biochem. J. (1967) vol. 105 pp. 1075–1083.
The Use of Trifluoroethanol for Improved Coupling in Solid-Base Peptice Synthesis by D. Yamashiro et al. in Tetrahedron Letters No. 18, pp. 1469–1472, 1976.

Primary Examiner—Christine M. Nucker
Attorney, Agent, or Firm—Phillips, Moore, Lempio & Finley

[57] ABSTRACT

A fully steroidogenically active analog of ACTH is disclosed. The analog differs from natural ACTH in that phenylalanine replaces tyrosine in the second position on the peptide chain; and norleucine replaces methionine in the fourth position on the peptide chain. The analog may be iodinated to yield [I]Tyr$^2$-Phe$^2$,Nle$^4$-ACTH, which also retains full steroidogenic activity. When labeled with iodine-125 the analog is useful in following steroidogenic processes and also in radioimmunoassays for ACTH.

18 Claims, No Drawings

BIOLOGICALLY ACTIVE ANALOGS OF ACTH AND RADIOIMMUNO ASSAY THEREFOR

The invention described herein was made in the course of, or under, a grant from the National Institutes of Health.

DESCRIPTION

1. Field of the Invention

The present invention relates generally to analogs of the hormone, corticotropin (ACTH), and more especially to analogs of ACTH which exhibit biological activity commensurate with that of native ACTH itself. Such analogs, unlike ACTH, exhibit full biological activity when reacted with radioiodine to form the radiolabeled compound, specifically, the radio-iodinated ACTH analog. The radio-iodinated analog may be assayed in a radioimmunological procedure which is useful in assessing the physiological functions of ACTH in its interactions with the adrenal gland and other corticosteroid producing functions.

2. Background of the Invention

Corticotropin, also known as adrenocorticotripic hormone (ACTH) is a primary hormone secreted by the pituitary gland, and it is responsible as mediator in the genesis of a variety of vital growth and physiological control steroids. Human ACTH is a polypeptide having 39 amino acid moieties in the following sequence:

H-Ser$^1$-Tyr-Ser-Met-Glu$^5$-His-Phe-Arg-Trp-Gly$^{10}$-Lys-Pro-Val-Gly-Lys$^{15}$-Lys-Arg-Arg-Pro-Val$^{20}$-Lys-Val-Tyr-Pro-Asn$^{25}$-Gly-Ala-Glu-Asp-Glu$^{30}$-Ser-Ala-Glu-Ala-Phe$^{35}$-Pro-Leu-Glu-Phe$^{39}$-Oh.

wherein:
Ala = alanine
Asp = aspartic acid
Asn = asparagine
Arg = arginine
Gly = glycine
Glu = glutamic acid
His = histidine
Lys = lysine
Leu = leucine
Met = methionine
Pro = proline
Phe = phenylalanine
Ser = serine
Trp = tryptophane
Tyr = tyrosine
Val = valine all of which are the common abbreviations for the various amino acid residues which appear in peptide molecules. H- and -OH indicate the orientation of the amino acid moieties in the peptide chain, i.e., H- indicates the amino functional end; and -OH indicates the carboxylic acid end.

For purposes of brevity, normal human corticotropin will hereafter be abbreviated as ACTH-(1-39). Where the final amino acid moiety, Phe is absent from the peptide, the abbreviation will be ACTH-(1-38), etc. Thus the numbers in parenthesis indicate the sequential number of amino acid moieties in the referenced molecule. It will be further understood that various fragments of ACTH-(1-39) are capable of exhibiting steroidogenic activity, and in some instances the activity of the fragment is, in all major aspects, essentially identical to the complete molecule, ACTH-(1-39). Thus, for ease in manipulation, synthesis, etc., the smaller fragment is often utilized in place of the complete 39 amino acid sequence. In this invention, ACTH-(1-38) was utilized in the studies; however, such ACTH-(1-38) exhibits in vitro and in vivo physiological activity essentially identical with normal ACTH-(1-39).

The role of ACTH in steroidogenesis in mammalian systems has been studied for many years in an effort to unravel the complex physiological functions of the steroids. One of the most powerful techniques in such studies is the use of radioisotopes which are incorporated into the various physiologically active molecules. The preparation of the radio labeled molecules permits a very accurate assessment of the physiological pathways followed by the molecules and their sequelae since the presence of the radioactive atoms can be detected in extremely low concentrations.

In principle, these labeling techniques could be very advantageously applied in studies of steroid generating processes. However, when the preferred radioisotope, iodine 125 ($^{125}$I) is incorporated into natural ACTH, biological activity is severely curtailed. For instance, McIlhinney and Schulster (Endocrinology 94:1259 (1974) prepared [$^{125}$I]ACTH by a lactoperoxidase process. This $^{125}$I labelled ACTH exhibited only 50% of the steroidogenic activity of the natural ACTH. Yanagibashi et al. (Endocrinol Japon 25:545 (1978)) also reported on the use of [$^{125}$I]ACTH in binding studies with isolated rat adrenocortical cells. However, they provided no characterization of the radio ligand, although loss of activity was noted.

Lemaire et al. (J. Amer. Chem. Soc. 99:1577 (1977)) found that where 3,5-diiodo tyrosine was substituted for normal tyrosine in the second amino acid position on natural ACTH-(1-39), the resultant molecule had a steroidogenic potency of 2.4% of the natural molecule. However, where 3,5-diiodo tyrosine was substituted for tyrosine which occupies the 23rd amino acid position on natural ACTH-(1-39), the resultant diiodo molecule was 64% as potent as the native hormone. Lowry et al. (J. Endocrinology 59:43 (1973)) who also studied iodo derivatives of ACTH-(1-24) reported similar losses in activity.

This loss of activity of radio-iodinated ACTH has interfered with studies directed to the elucidation of the steroidogenic pathways including the physiologically relevant corticotropin receptors and receptor sites; and in the detection of ACTH in radioimmuno assaying techniques. This activity loss is apparently connected with the distortion of the ACTH geometry occasioned by the introduction of the iodine atoms at sensitive sites within the amino acid peptide sequence.

It is therefore of interest to prepare analogs of ACTH which retain their full steroidogenic activity when radio-ligands are introduced into the ACTH peptide.

BRIEF DESCRIPTION OF THE INVENTION

ACTH analogs have been prepared which exhibit full biological activity. Importantly, the biological activity of the ACTH analogs of the invention remains fully comparable to native ACTH even when radioligands, specifically radio-iodine, are introduced into the ACTH analogs. These radio-iodinated analogs are also useful in radioimmuno assay procedures to detect and quantify the presence of ACTH in biological systems.

More specifically, it has been determined that two amino acid moieties, i.e., phenylalanine and norleucine (abbreviated as "Nle") may be substituted for tyrosine in the second amino acid position, and for methionine in the fourth amino acid position in the native ACTH peptide sequence, respectively, without interference with the biological activity of ACTH peptide. This analog will be referred to herein as [Phe$^2$,Nle$^4$] ACTH, thus signifying that phenylalanine, rather than tryrosine, appears in the second position on the peptide; and that norleucine, rather than methionine, appears in the fourth position on the peptide.

It has also been determined that the analog [Phe$^2$,-Nle$^4$]-ACTH may be iodinated with the radioisotope, $^{125}$I, to produce a radio labeled derivative, [$^{125}$I]-Tyr$^{23}$,-Phe$^2$,Nle$^4$-ACTH. The radio-iodinated derivative of the analog Phe$^2$Nle$^4$-ACTH also remains fully biologically active.

A radioimmunoassay has also been devised using the [$^{125}$I]-Tyr$^{23}$,Phe$^2$,Nle$^4$-ACTH analog. In this assay the radio-labeled ACTH is incubated with ACTH antiserum produced from previously injected and sensitized rabbits.

It is an object of the invention to provide fully biologically active analogs of ACTH.

It is another object of the invention to provide radiolabeled fully biologically active analogs of ACTH.

It is yet another object of the invention to provide a biologically active ACTH analog, Phe$^2$,Nle$^4$-ACTH.

It is still another object of the invention to provide a biologically active radio-iodine labeled ACTH analog.

It is still another object of the invention to provide a radio-iodine 125 labeled ACTH analog, [$^{125}$I]-Tyr$^{23}$,-Phe$^2$,Nle$^4$-ACTH.

It is yet another object of the invention to provide a radioimmunoassay for ACTH.

Additional objects, advantages and novel features of the invention are set forth in the following description, and in part will become apparent to those skilled in the art upon examination of the following, or may be learned by practice of the invention. The objects and advantages of the invention may be realized and attained by means of the instrumentalities and combinations particularly set forth in the appended claims.

DETAILED DESCRIPTION OF THE INVENTION

The ACTH Analog

An analog of ACTH that exhibits full steroidogenic activity is produced when two of the naturally occuring amino acid moieties in ACTH are replaced by alternate amino acids.

Specifically, the tyrosine moiety occuring in the second position in natural ACTH is replaced by the amino acid, phenylalanine. These amino acids are closely related, with the difference being that a hydroxyl group which is attached to the terminal phenyl group on tyrosine does not exist in phenylalanine, which terminates in a simple phenyl group. Thus phenylalanine has the formula:

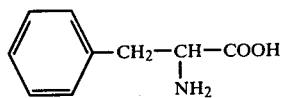

while tyrosine has the formula:

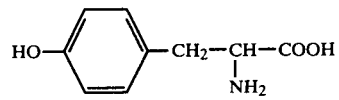

A second amino acid moiety, namely methionine, that occurs in the fourth position in natural ACTH is replaced by the amino acid norleucine. Methionine and norleucine are not as closely related as are tyrosine and phenylalanine, since norleucine does not contain the sulphur atom which occurs in the methionine molecule. Norleucine has the formula:

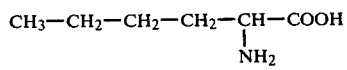

while methionine has the formula:

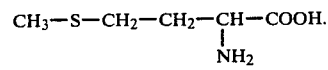

The fully active ACTH analog therefore has the following peptide sequence:

H-Ser$^1$-Phe-Ser-Nle-Glu$^5$-His-Phe-Arg-Trp-Gly$^{10}$-Lys-Pro-Val-Gly-Lys$^{15}$-Lys-Arg-Arg-Pro-Val$^{20}$-Lys-Val-Tyr-Pro-Asn$^{25}$-Gly-Ala-Glu-Asp-Glu$^{30}$-Ser-Ala-Glu-Ala-Phe$^{35}$-Pro-Leu-Glu-Phe$^{39}$-OH.

The biologically active analog, Phe$^2$,Nle$^4$-ACTH-(1-38), may be prepared by solid phase synthesis starting with a brominated polymer containing the human ACTH sequence 7-38. This protected peptide resin may be prepared as described by Li et al. in the Proceedings of The National Academy of Sciences USA 75:4306 (1978), which preparation is incorporated herein by reference for the synthesis of ACTH-(7-38). Addition of side chain protected His, Glu, Nle, Ser, Phe and Ser in a stepwise manner to the ACTH-(7-38) peptide resin by a symmetrical anhydride coupling procedure yields protected Phe$^2$,Nle$^4$-ACTH-(1-38) resin quantitatively.

The free peptide is removed from the resin by treatment with liquid HF which also removes all the protecting groups except the formyl group on the indole of the tryptophan residue. This protective group is removed by brief incubation at pH 11.5.

The peptide is purified by chromatography on carboxymethyl cellulose. The peptide in the major peak is isolated and further purified by partition chromatography on Sephadex G-50.

Phe$^2$, Nle$^4$-ACTH-(1-38) is obtained as a final product after partition chromatography. A 10% overall yield based on starting resin is normally observed.

This preparation may be more clearly apparent from the following Example:

EXAMPLE I

Preparation of Biologically Active Analog

The biologically active analog Phe$^2$, Nle$^4$-ACTH(1-38) was synthesized by adding protected amino acid residue to resin containing the side-chain protected amino acid sequence corresponding to residues 7-38 of human ACTH. The synthesis of the protected ACTH (7-38) resin has been described previously by Li et al. (see reference above). Addition of the remaining six amino acid residues (corresponding to the sequence Ser-Phe-Ser-Nle-Glu-His) was performed according to procedures previously outlined by Yamashiro et al. in Tetrahedron Letters 18:1469 (1976); wherein trifluoroethanol was used to couple peptides in solid phase. Such disclosure is also incorporated herein by reference. The hydroxyl group of serine and the γ-carboxyl group of glutamic acid were protected with the benzyl group. A benzyloxycarbonyl group was used to protect the imidazole group of histidine. Reversible protection of the α-amino group was accomplished by the use of the t-butyloxycarbonyl (BOC) group. Symmetrical anhydride coupling was employed (3 equivalents per equivalent of original load on resin). $Phe^2$, $Nle^4$-ACTH-(1-38) resin was obtained in quantitative yield (0.994 g) starting with 0.885 g ACTH-(7-38) resin.

A sample (0.5 g) was treated with 10 ml liquid HF in the presence of 1 ml anisole at 0° for 75 min. After removal of HF and washing with ethyl acetate, the peptide was extracted with 0.5 N acetic acid and filtered through Sephadex G-10 in 0.5 N acetic acid. The yield was 175 mg. This product was then dissolved in 10 ml water and the pH was raised to 11.4 by the addition of 0.1 N NaOH (5 ml) for 2 min and then acidified to pH 4.5 with 0.1 N acetic acid. This effected deformylation of the blocked tryptophan residue.

$Phe^2$, $Nle^4$-ACTH-(1-38) was purified by ion exchange chromatography on carboxymethyl cellulose followed by partition chromatography on Sephadex G-50 in the solvent 1-butanol:pyridine:0.1% acetic acid. 5:3:11 v/v.

$Phe^2$, $Nle^4$-ACTH-(1-38) product was found to be homogeneous by thin layer chromatography on silica gel G in the solvent 1-butanol:pyridine:acetic acid:$H_2O$; 5:5:1:4 v/v ($R_f$ 0.38) and by paper electrophoresis at pH 3.7 ($R_f^{Lys}$ 0.57) and pH 7 ($R_f^{Lys}$ 0.21). The amino acid composition of an acid hydrolysate of the peptide agreed well with that expected for $Phe^2$, $Nle^4$-ACTH-(1-38) (see Table I below).

TABLE I

Amino Acid Composition of $Phe^2$, $Nle^4$-ACTH-(1-38)

| Amino acid | Theoretical | Found |
|---|---|---|
| Trp | 1 | 0.94 |
| His | 1 | 1.02 |
| Lys | 4 | 4.00 |
| Arg | 3 | 3.29 |
| Asp | 2 | 1.95 |
| Ser | 3 | 2.69 |
| Glu | 5 | 5.37 |
| Pro | 4 | 3.81 |
| Gly | 3 | 2.99 |
| Ala | 3 | 2.82 |
| Val | 3 | 2.86 |
| Nl3 | 1 | 0.92 |
| Leu | 1 | 1.16 |
| Tyr | 1 | 0.88 |
| Phe | 3 | 2.78 |

$Phe^2$, $Nle^4$-ACTH-(1-38) (0.5 mg) was hydrolyzed for 18 hr. with 0.2 ml 4 N methane sulfonic acid at 110° and the digest analyzed on a Beckman 119-C analyzer.

The peptide content of the final product obtained after partition chromatography was found to be 90% by ultraviolet spectral analysis.

The biological activity of $Phe^2$, $Nle^4$-ACTH-(1-38) was found to be indistinguishable from that of synthetic human ACTH. $Phe^2$, $Nle^4$-ACTH stimulated corticosterone production in isolated rat adrenocortical cells to the same maximal degree as human ACTH. It was apparent from the results that $Phe^2$, $Nle^4$-ACTH-(1-38) is as potent as ACTH in stimulating steroidogenesis.

The Iodinated ACTH Analog

The removal of tyrosine from the second amino acid position in natural ACTH and its replacement by phenylalanine enables the preparation of iodinated derivatives wherein iodine addition is restricted to the tyrosine residue at the twenty-third position. Restricting iodine addition to the 23rd amino acid in the ACTH sequence, removes the iodine from the highly biologically sensitive portion (1-18) and places it in the much less sensitive portion (19-38) of the peptide.

$Phe^2$,$Nle^4$-ACTH-(1-38) may be iodinated with KI after dissolving the ACTH peptide analog in borate buffer (pH 9) at 0° in the presence of guanidine HCl. The iodo derivatives can be separated by reverse phase high performance liquid chromatography (HPLC). The materials in the elution peaks may be identified by ultraviolet difference spectroscopy at pH 12 vs pH 3. The characteristic shifts of the absorption maximum of ionized tryosyl residue from 294 nm to 305 nm for monoiodo- and 311 nm for diiodo-tryosyl residues are observed for the peptides in the second and third peaks, respectively. The first peak contains unmodified $Phe^2$,-$Nle^4$-ACTH-(1-38).

Partition chromatography in the solvent 1-butanol:pyridine:0.1% acetic acid provides excellent separation of $Phe^2$, $Nle^4$-ACTH-(1-38) from the iodo derivatives but does not separate the monoiodo from the diiodo dervative. Reverse phase HPLC provides complete separation of all three components in a short time.

The steriodogenic potency of the monoiodo derivative of $Phe^2$,$Nle^4$-ACTH-(1-38) was measured using isolated rat adrenocortical cells. It is obvious that the monoiodo derivative of $Phe^2$ $Nle^4$-ACTH-(1-38) is also equipotent with ACTH. Non-linear least squares analysis of the data showed that the concentrations of ACTH and the monoiodo derivative of $Phe^2$, $Nle^4$-ACTH-(1-38) required for half maximal stimulation of steroidogenesis are 36.5±6.1 pM and 37.6±6.8 pM, respectively.

Further details of preparation of iodinated ACTH analog will be apparent from Example II below:

EXAMPLE II

Iodination of $Phe^2$, $Nle^4$-ACTH-(1-38)

Two mg of $Phe^2$, $Nle^4$-ACTH-(1-38) was dissolved in 1 ml 0.2 M borate buffer, pH 9, containing 1 M guanidine HCl. A solution of 0.01 M iodine in KI (0.06 ml) was added to the peptide with stirring at 0°. The reaction was quenched after 3 min. by the addition of 0.05 mg dithiothreitol. The iodinated peptide was then purified by reverse phase high performance liquid chromatography (HPLC) on an Altex RP-18 column (0.4×25 cm) by isocratic elution with 16% 1-propanol in 1 M pyridine acetate, pH 5.5.

HPLC was performed using a system composed of high pressure Milton Roy minipump (Glenco, Houston, Texas) and a sample injection valve with a 0.02 ml or 1 ml loop (Rheodyne, Berkley, Calif.). The column effluent was monitored automatically with fluorescamine using a stream sampling technique.

The $R_f$ values of $Phe^2$, $Nle^4$-ACTH-(1-38) and its iodo derivates are compared with those of human ACTH in Table II below.

TABLE II

R_f values of Phe$^2$, Nle$^4$-ACTH (1-38) and its iodo derivatives.

| Peptide | TLC$^a$ | HPLC$^b$ | Partition chromatography$^c$ |
|---|---|---|---|
| ACTH | 0.26 | — | 0.25 |
| Phe$^2$, Nle$^4$-ACTH(1-38) | 0.38 | 0.15 | 0.27 |
| Monoiodo Tyr$^{23}$, Phe$^2$, Nle$^4$-ACTH(1-38) | 0.40 | 0.13 | 0.45 |
| DiiodoTyr$^{23}$, Phe$^2$, Nle$^4$-ACTH(1-38) | — | 0.10 | 0.45 |

$^a$Tlc was performed on silica gel G in the solvent 1-butanol:pyridine:acetic pyridine:acetic acid:water, 5:5:1:4 (v/v)
$^b$HPLC was performed on Altex RP-18 using isocratic elution with 16% 1-propanol in 1M pyridine acetate, pH 5.5.
$^c$Partition was performed on Sephadex G-50 in the solvent 1-butanol:pyridine:0.1% acetic acid, 5:3:11 (v/v)

Example III below sets forth suitable methods for determining biological activity of the ACTH analogs.

EXAMPLE III

Determination of Biological Activity

Biological activities of the peptides were determined by isolated rat adrenocortical cell assay as previously described by Lee et al. in Archives Biochem. Biophysics 201:411 (1980). In this assay, adrenocortical cells isolated from the decapsulated adrenals of adult male Sprague-Dawley rats by collagenase treatment, are incubated with various concentrations of the peptides in medium 199 containing 10% fetal bovine serum at 37° for 1 hr. Corticosterone production is estimated by a specific radioimmunoassay as described by Rao et al. in Endocrinology 102:371 (1978).

The Radio-iodine Labeled ACTH Analog

As discussed above, the iodinated analog of Phe$^2$,-Nle$^4$-ACTH, exhibits full steroidogenic activity commensurate with the activity of the analog Phe$^2$,Nle$^4$-ACTH and with natural ACTH itself.

A radio-iodine labeled analog otherwise identical in all respects with [I]-Phe$^2$,Nle$^4$-ACTH described above may also be prepared and thereafter utilized in a radioimmunoassay. The radioiodine [$^{125}$I] isotope may be introduced into Phe$^2$,Nle$^4$-ACTH by a chloramine-T procedure. This procedure may best be understood from a review of Example IV below.

EXAMPLE IV

Preparation of [$^{125}$I]-TYR$^{23}$,Phe$^2$,Nle$^4$-ACTH (1-38)

Introduction of [$^{125}$I] into Phe$^2$,Nle$^4$-ACTH (1-38) was accomplished by the use of chloramine-T as follows. 5 μg of peptide was dissolved in 5 μl of 0.2 M phosphate buffer (pH 7.6) and diluted with 25 μl of 0.5 M phosphate buffer (pH 7.8). The following solutions were added in order at 20 second intervals, with mixing: Na$^{125}$I, 2 mCi (3 μl); 0.35% chloramine-T (6 μl); 10% β-mercaptoethylamine (20 μl).

After the last addition, the reaction mixture was chromatographed on Sephadex LH-20 in the solvent 1 M pyridine acetate, pH 5.5, containing 3% ethanol and 1% β-mercaptoethanol. The fractions containing the excluded peak of radioactivity were stored at 4° and aliquots were freshly purified by reverse phase high performance liquid chromatography (HPLC) on an Altex Lichrosorb C-8 column (0.4×25 cm) just prior to use in radioimmunoassay.

The HPLC system considered of a Milton-Roy minipump connected to Rheodyne 9125 injector with a 1 ml loop and the Altex column. Fractions were collected and 10 μl aliquots were directly counted in a Beckman Gamma 4000 counter at 60% efficiency.

The [$^{125}$I]-Phe$^2$Nle$^4$-ACTH (1-38) analog is useful in a radioimmunoassay procedure which is highly sensitive. This procedure may best be understood by a review of the following Example V.

EXAMPLE V

Radioimmunoassay

An ACTH antiserum was prepared as follows:

Highly purified porcine ACTH (1-39) was coupled to bovine serum albumin (BSA) by the carbodiimide procedure. By adding 1×10$^6$ cpm [$^3$H]-ACTH to the reaction mixture, the incorporation of ACTH into BSA was found to be 6.8 moles ACTH/mole BSA.

Three month old male New Zealand white rabbits were injected with 40×10$^9$ heat-killed Bordetella pertussis organisms (DIFCO) intradermally in 0.5 ml at 10 sites on the rump. Ten days later, 2 ml of the immunization mixture containing 100 μg hapten was injected intradermally over the shoulder at 40 sites. The immunization mixture was prepared according to the method set forth by Vaitukaitis et al. in J. Climinical Endocrinology Metabolism 33:988 (1971).

Animals were boosted at 2 and 4 weeks following the primary injection with 20 μg hapten in Freund's incomplete adjuvant and phosphate buffered saline (1:1). Titers were followed throughout by bleeding 1–2 ml and assaying for ACTH antibodies by radioimmunoassay (RIA). Ten days after boosting at week 5, animals were bled and 30 ml blood was collected. The sera were separated, assayed for titer and then lyophilized. No loss of titer was observed following lyophilization. The lyophilized antisera were stored at −20°. Titers continued to rise for 120 days folloing primary immunization.

Saturation curves for ACTH antisera using [$^3$H]-ACTH or [$^{125}$I]-Tyr$^{23}$,Phe$^2$,Nle$^4$-ACTH (1-38) as the radioligand were generated by the following procedure. The assay buffer consisted of 0.05 M phosphate buffer, pH 7.4, containing 0.25% BSA, 0.5% β-mercaptoethanol and 0.01% polylysine (MW 15,000, Sigma). Varying amounts of labeled ACTH were incubated with the antiserum at a final dilution of 1:58,000 in a total volume of 200 μl for 2 hr. at room temperature. Blanks containing no antiserum were included for each point.

Protein A immunoprecipitant (Bethesda Research Labs.) was washed according to Kessler's method set forth in the Journal of Immunology 115:1617 (1975), and then resuspended in assay buffer at a dilution of 1:8. 25 μl of this washed protein A immunoprecipitant was added and the incubation was continued at 4° for 18 hr. One ml of assay buffer at 4° was added to a series of tubes and the tubes were then centrifuged at 2500 rpm for 15 min in a Beckman model TJ-6 refrigerated centrifuge. The supernatant was poured off, the tubes drained, the sides of the tubes wiped with cotton and then the tubes were counted directly in a Beckman Gamma 4000 counter for [$^{125}$I].

The tubes containing [$^3$H]-ACTH were processed similarly, drained, wiped and then 0.5 ml 0.1 N NaOH was added. The tubes were stirred on a Vortex mixer for 20 sec. and incubated at 37° for 30 min. An aliquot (0.4 ml) of the NaOH extract was mixed with phase combininhg scintillant (PCS, Amersham) and counted in a Packard PRIAS scintillation counter. The counting efficiency was 30%.

Standard radioimmunoassays were performed as follows: Unlabeled ACTH or other peptides in a volume of 50 μl were mixed with 50 μl antiserum and 50 μl Protein A immunoprecipitant washed as described above. All components were prepared in assay buffer and incubated at 4° for 24 hr. [$^{125}$I]-Tyr$^{23}$,Phe$^2$,Nl3$^4$-ACTH (-38) (10,000 cpm) in 50 μl assay buffer was added and incubation continued for another 24 hr. at 4°. One ml of assay buffer was added and the tubes were processed as described above for counting in the Beckman 4000 counter.

From saturation curves the affinity of the antiserum for ACTH could be determined. Nonlinear least squares analysis of the data showed that the apparent dissociation constant for the interaction of ACTH with antiserum 46-1 is 96±16 pM. This gives a value of $1 \times 10^{10}$ $M^{-1}$ for the association constant. Antiserum was seen to have high affinity for ACTH.

The RIA is capable of detecting as little as 1 picogram of ACTH.

More specifically, the antiserum has high affinity for ACTH as indicated by binding curves derived from the procedures. Because of this high affinity ($K_D = 1 \times 10^{10}$ $M^{-1}$) is was possible to develop a highly sensitive RIA for ACTH using antiserum. There are several important features of this RIA for ACTH. Firstly, the radioligand is a homogeneous product with full biological activity and theoretical radioactivity. Secondly, the radioligand, [$^{125}$I]-Tyr$^{23}$, Phe$^2$, Nl3$^4$-ACTH (1-38), is immunochemically equivalent to ACTH against which the antiserum was raised. The displacement curves of ACTH and nonradioactive monoiodo Tyr$^{23}$,Phe$^2$,Nle$^4$-ACTH (1-38) are identical. Furthermore, 50% displacement of the radioligand was produced by one equivalent of the unlabeled hormone whereas several fold excess of unlabeled hormone is usually required for 50% displacement.

Owing to the high affinity of the antiserum for ACTH, it was possible to increase the sensitivity of the assay by preincubating the unlabeled hormone with the antiserum. This increase in sensitivity is readily apparent from a comparison of the concentration needed for half-maximal binding of the radioligand, 96±16 pM, with the value for 50% displacement of radioligand, 20.3±3.3 pM. The latter assay involved preincubation of the antiserum with the competing peptide. Under the preincubation conditions, less than one equivalent of unlabeled ACTH was needed for 50% displacement. Using antiserum at a dilution of 1:58,000 and 10,000 cpm of [$^{125}$I]-Tyr$^{23}$,Phe$^2$,Nle$^4$-ACTH (1-38), it was possible to detect 1 pg of ACTH by RIA. Since ACTH RIAs generally employ about 2000 cpm tracer, it should be possible to increase the sensitivity of this assay by using less tracer and higher dilution of the antiserum.

The biological activity of [$^{125}$I]-Tyr$^{23}$,Phe$^2$,Nle$^4$-ACTH (1-38) was measured by its ability to stimulate corticosterone production in isolated rat adrenocortical cells. The results showed that the steroidogenic potency of [$^{125}$I]-Tyr$^{23}$,Phe$^2$,Nle$^4$-ACTH (1-38) is indistinguishable from that of ACTH. The concentrations required for half-maximal stimulation of steroidogenesis of two separate preparations of [$^{125}$I]-Tyr$^{23}$,Phe$^2$,Nle$^4$-ACTH (1-38) were 36.5±6.1 pM and 40.7±6.9 pM compared to a value of 37.6±6.7 pM for ACTH.

This radioligand, [$^{125}$I]-Tyr$^{23}$,Phe$^2$Nle$^4$-ACTH (1-38), with full biological activity and near theoretical radioactivity is a suitable tracer for use in the identification of physiologically relevant receptors for ACTH on adrenocortical cells as well as other target cells.

We claim:

1. A steroidogenically active polypeptide and analog of corticotropin having the formula:
   H-Ser-Phe-Ser-Nle-Glu-His-Phe-Arg-Trp-Gly-Lys-Pro-Val-Gly-Lys-Lys-Arg-Arg-Pro-Nal-Lys-Val-Tyr-Pro-Asn-Gly-Ala-Glu-Asp-Glu-Ser-Ala-Glu-Ala-Phe-Pro-Leu-Glu-Phe-OH.

2. The composition of claim 1 wherein the polypeptide is shortened by one or more amino acid moieties at the -OH end.

3. The composition of claim 2 wherein the polypeptide is shortened by one amino acid moiety at the -OH end.

4. The corticortropin analog of claim 1 wherein the polypeptide further includes at least one iodine atom in the polypeptide chain.

5. The corticotropin analog of claim 4 wherein the iodine atom is attached to the Tyr amino acid moiety.

6. The corticotropin analog of claim 1 wherein the polypeptide incorporates a radioisotope.

7. The corticotropin analog of claim 6 wherein the radio-isotope is attached to the Tyr amino acid moiety.

8. The corticotropin analog of claim 7 wherein the radioisotope is iodine-125.

9. The corticotropin analog of claim 2 wherein the polypeptide incorporates a radioisotope.

10. The cortiotropin analog of claim 9 wherein the radio-isotope is attached to the Tyr amino acid moiety.

11. The corticotropin analog of claim 9 wherein the radio-isotope is iodine-125.

12. A method for investigating the reactive pathways of corticotropin in biological systems comprising substituting a radio-isotope labeled polypeptide, [$^{125}$I]-Tyr$^{23}$-Phe$^2$Nle$^4$-ACTH for natural ACTH in the biological system.

13. In an immunological method for assaying ACTH, the step of utilizing a radioisotope labeled ACTH analog as an antigen.

14. The assay method of claim 13 wherein the radioisotope labeled ACTH analog is labeled with iodine-125.

15. The method of claim 13 wherein the radio-isotope labeled ACTH analog is [$^{125}$I]-Tyr$^{23}$-Phe$^2$-Nle$^4$-ACTH.

16. The method of claim 13 wherein the radio-isotope labeled ACTH analog is [$^{125}$I]-Tyr$^{23}$-Phe$^2$,Nle$^4$-ACTH (1-38).

17. A method for producing a steroidogenically active peptide analog of ACTH comprising attaching a phenylalaninyl moiety in the second position on the peptide chain between the first and third serinyl moieties and attaching a norleucinyl moiety in the fourth position on the peptide chain between the third serinyl moiety and the fifth glutamic acid moiety.

18. A method for producing a radioisotope labeled analog of ACTH comprising reacting a polypeptide Phe$^2$,Nle$^4$-ACTH with a salt of iodine-125 to react said salt with said peptide and produce the radio-isotope labeled analog, [$^{125}$I]-Tyr$^{23}$-Phe$^2$,Nle$^4$-ACTH.

* * * * *